US009539009B2

(12) United States Patent
Hoke et al.

(10) Patent No.: US 9,539,009 B2
(45) Date of Patent: Jan. 10, 2017

(54) BIOLOGICAL TISSUE CONNECTION AND REPAIR DEVICES AND METHODS OF USING SAME

(71) Applicant: The Johns Hopkins University, Baltimore, MD (US)

(72) Inventors: Ahmet Hoke, Townson, MD (US); Hai-Quan Mao, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/098,964

(22) Filed: Dec. 6, 2013

(65) Prior Publication Data

US 2014/0163589 A1 Jun. 12, 2014

Related U.S. Application Data

(63) Continuation of application No. 13/255,882, filed as application No. PCT/US2010/026872 on Mar. 10, 2010, now abandoned.

(60) Provisional application No. 61/159,012, filed on Mar. 10, 2009.

(51) Int. Cl.
| | |
|---|---|
| *A61B 17/08* | (2006.01) |
| *A61B 17/11* | (2006.01) |
| *A61B 17/00* | (2006.01) |
| *A61L 31/14* | (2006.01) |
| *A61F 2/00* | (2006.01) |

(52) U.S. Cl.
CPC ......... *A61B 17/11* (2013.01); *A61B 17/00491* (2013.01); *A61B 17/1128* (2013.01); *A61F 2/0063* (2013.01); *A61L 31/14* (2013.01); *A61B 2017/00004* (2013.01); *A61B 2017/00526* (2013.01); *A61B 2017/00893* (2013.01); *A61B 2017/00951* (2013.01); *A61B 2017/1107* (2013.01); *A61B 2017/1132* (2013.01)

(58) Field of Classification Search
CPC ................. A61B 17/11; A61B 17/1128; A61B 2017/1132; A61F 2/0063
USPC ........ 606/153, 154, 213, 214; 623/1.1, 1.23, 623/1.27, 1.36, 1.38, 1.39, 1.41, 1.44, 1.46, 623/1.48, 1.54, 11.11, 13.11, 13.15, 13.17, 623/23.64, 23.71; 600/36
See application file for complete search history.

(56) References Cited

U.S. PATENT DOCUMENTS

| | | | | |
|---|---|---|---|---|
| 3,254,650 | A | * | 6/1966 | Collito .......................... 606/153 |
| 3,916,905 | A | * | 11/1975 | Kuhn ............................ 606/152 |
| 3,960,151 | A | * | 6/1976 | Kuhn ............................ 606/152 |
| 4,470,415 | A | | 9/1984 | Wozniak |
| 4,778,467 | A | | 10/1988 | Stensaas et al. |

(Continued)

FOREIGN PATENT DOCUMENTS

| | | |
|---|---|---|
| DE | 10205997 A1 | 9/2003 |
| JP | S60-500485 A | 4/1985 |

(Continued)

OTHER PUBLICATIONS

European Search Report dated Nov. 30, 2015 in European Application No. 10751380.6.

*Primary Examiner* — Robert Lynch
(74) *Attorney, Agent, or Firm* — Mintz Levin Cohn Ferris Glovsky and Popeo, P.C.; Peter F. Corless, Esq.; Daniel W. Clarke

(57) ABSTRACT

The instant invention provides compositions and methods for promoting the repair and/or growth of biological tissue, e.g., tubular biological tissue such as nerves. Specifically, the instant invention provides tissue connection devices and tissue repair devices and methods for using these devices.

14 Claims, 7 Drawing Sheets

(56) References Cited

U.S. PATENT DOCUMENTS

| | | | | |
|---|---|---|---|---|
| 4,883,618 A | * | 11/1989 | Barrows | 264/49 |
| 5,011,486 A | * | 4/1991 | Aebischer et al. | 623/1.15 |
| 5,030,225 A | * | 7/1991 | Aebischer et al. | 606/152 |
| 5,092,871 A | * | 3/1992 | Aebischer et al. | 606/152 |
| 5,487,756 A | * | 1/1996 | Kallesoe | A61N 1/0556 600/381 |
| 5,718,973 A | * | 2/1998 | Lewis | A61F 2/82 428/35.7 |
| 2005/0021034 A1 | | 1/2005 | Cohen et al. | |
| 2005/0183731 A1 | | 8/2005 | Hunter et al. | |
| 2006/0089646 A1 | * | 4/2006 | Bonutti | 606/61 |
| 2007/0250114 A1 | | 10/2007 | Drapeau | |
| 2008/0109070 A1 | | 5/2008 | Wagner et al. | |
| 2008/0262519 A1 | | 10/2008 | Gurtner et al. | |
| 2011/0059150 A1 | | 3/2011 | Kendall et al. | |

FOREIGN PATENT DOCUMENTS

| | | |
|---|---|---|
| JP | 11-033104 A | 2/1999 |
| JP | 2939750 B2 | 8/1999 |
| JP | 2000510712 A | 8/2000 |
| JP | 2004136097 A | 5/2004 |
| JP | 2006505305 A | 2/2006 |
| JP | 2006508709 A | 3/2006 |
| JP | 2006-110184 A | 4/2006 |
| JP | 2006516202 A | 6/2006 |
| KR | 100687487 B1 | 2/2007 |
| WO | WO-84/03035 A1 | 8/1984 |
| WO | WO-88/06871 A1 | 9/1988 |
| WO | WO-90/05552 A1 | 5/1990 |
| WO | WO-9312724 A1 | 7/1993 |
| WO | WO2004/094303 A2 | 11/2004 |
| WO | WO-2005002472 A1 | 1/2005 |
| WO | WO2006/123340 A2 | 11/2006 |
| WO | WO2007149982 A2 | 12/2007 |

* cited by examiner

BIOLOGICAL TISSUE CONNECTION AND REPAIR DEVICES AND METHODS OF USING SAME

RELATED APPLICATIONS

This application is a continuation application of U.S. Ser. No. 13/255,882, filed Nov. 21, 2011, which is a national stage application filed under 35 U.S.C. §371 of international application no. PCT/US2010/026872, filed Mar. 10, 2010, which claims the benefit of priority under 35 U.S.C. §119(e) to U.S. Provisional Application No: 61/159,012, filed Mar. 10, 2009, each of which is incorporated herein by reference in its entirety.

BACKGROUND OF THE INVENTION

One of the main challenges during repairs of tubular organs such as nerves, blood vessels and tendons is reattachment of the severed or injured ends of the nerve, blood vessel or tendon using microsurgical techniques. Placing micro-sutures is time consuming and prolongs the duration that the patient is under anesthesia. Furthermore, placement of sutures, even micro-sutures, may result in further injury to the nerve, blood vessel, tendon, lymphatic vessel, digestive tract or genitourinary tract and thus delay recovery or impair the degree of recovery.

Accordingly, it is necessary in the art to obviate the use of sutures when repairing biological tissue, e.g., tubular biological tissues.

SUMMARY OF THE INVENTION

The instant invention provides compositions and methods for promoting the repair and/or growth of biological tissue, e.g., tubular biological tissue such as nerves. The compositions and methods of the invention can be employed to restore the continuity of biological tissue interrupted by disease, traumatic events or surgical procedures.

Accordingly, in at least one aspect, the invention provides tissue connection devices for connecting biological tissue, comprising a first tubular device comprising a first and a second end; a second tubular device comprising a first and a second end; wherein one end of the first and second tubular devices attach to the ends of the biological tissue, and the other ends of the first and second tubular devices attach to donor tissue.

In one embodiment, the tissue connection device comprises two or more sections that assemble to form the tubular device. In another embodiment, the sections are connected, or partially connected, e.g., along the length of one side of the sections.

In another embodiment, the tissue connection device comprise a biodegradable substrate.

In another embodiment, the interior surface of each section of the tubular device comprises an adhesive, a temperature sensitive polymer, adhesive nanostructure, or tissue-reactive groups. Exemplary adhesives include fibrin glue, cyanoacrylate tissue adhesive, and albumin-glutaraldehyde glue. Exemplary temperature sensitive polymer include poly (N-isopropyl acrylamide), and Pluronic copolymers. Exemplary tissue reactive groups include imido esters, N-hydroxysuccinimide esters, epoxides, isocyanates, and aldehydes. Exemplary nanostructures are pillars comprised of biodegradable material, e.g., pillars comprising diameters in the range of 50 nm to 5 microns and lengths in the range of 10 microns to 2 mm.

In one embodiment, the adhesive, temperature sensitive polymer, adhesive nanostructure, or tissue-reactive group attaches the device to the tubular tissue. In another embodiment, the adhesive further attaches the first section of the tubular device to the second section of the tubular device.

In another embodiment, the tubular devices comprise an inner diameter of 0.10-100 mm or 0.25-50 mm.

In another embodiment, the tubular devices have a thickness of 50-5000 µm, or 100-3000 µm.

In another embodiment, the devices tissue connection devices comprise one or more of biodegradable polyesters, poly(amino acids), poly(amino acid) derivatives, and natural polymers. Exemplary polyesters include poly(lactide), poly (glycolide), poly(ε-caprolactone) and copolymers thereof. Exemplary natural polymer include chitosan, collagen, alginate esters, hyaluronic acid and derivatives thereof.

In one embodiment, the tubular devices are porous or non-porous. In one embodiment, the porous device comprises a biodegradable foam or non-woven electrospun fibrous mesh. In another embodiment, the porous devices comprise a porous membrane with pore size of less than 100 microns, or less than 50 microns.

In one embodiment, the tissue connection devices comprise a non-woven electrospun fibrous mesh, in exemplary embodiments, the non-woven electrospun fibrous mesh comprises a fiber diameter from about 20 nm to about 2 microns. In another exemplary embodiment, the non-woven electrospun fibrous mesh comprises pore sizes ranging from about 200 nm to about 20 microns.

In one embodiment, the devices are biodegradable.

In another embodiment, the biological tissue is a tubular biological tissue, e.g., nerve, blood vessel, tendon, digestive tract, lymphatic, or genitourinary system tissue. An exemplary nerve tissue is peripheral nerve tissue. Exemplary genitourinary tissues are ureters or urethras.

In another aspect, the instant invention provides tissue connection devices comprising a tubular biodegradable structure, wherein the devices comprise two or more sections that assemble around the biological tissue to form the tubular device. In one embodiment, the sections are connected, or partially connected, e.g., along the length of one side of the sections.

In another embodiment, the tissue connection device comprise a biodegradable substrate.

In another embodiment, the interior surface of each section of the tubular device comprises an adhesive, a temperature sensitive polymer, adhesive nanostructure, or tissue-reactive groups. Exemplary adhesives include fibrin glue, cyanoacrylate tissue adhesive, and albumin-glutaraldehyde glue. Exemplary temperature sensitive polymer include poly (N-isopropyl acrylamide), and Pluronic copolymers. Exemplary tissue reactive groups include imide esters, N-hydroxylsuccinimide esters, epoxides, isocyanates, and aldehydes. Exemplary nanostructures are pillars comprised of biodegradable material, e.g., pillars comprising diameters in the range of 50 nm to 5 microns and lengths in the range of 10 microns to 2 mm.

In one embodiment, the adhesive, temperature sensitive polymer, adhesive nanostructure, or tissue-reactive group attaches the device to the tubular tissue. In another embodiment, the adhesive further attaches the first section of the tubular device to the second section of the tubular device.

In another embodiment, the tubular devices comprise an inner diameter of 0.10-100 mm or 0.25-50 mm.

In another embodiment, the tubular devices have a thickness of 50-5000 µm, or 100-3000 µm.

In another embodiment, the devices tissue connection devices comprise one or more of biodegradable polyesters, poly(amino acids), poly(amino acid) derivatives, and natural polymers. Exemplary polyesters include poly(lactide), polAglycolide), poly(ε-caprolactone) and copolymers thereof. Exemplary natural polymer include chitosan, collagen, alginate esters, hyaluronic acid and derivatives thereof.

In one embodiment, the tubular devices are porous or non-porous. In one embodiment, the porous device comprises a biodegradable foam or non-woven electrospun fibrous mesh. In another embodiment, the porous devices comprise a porous membrane with pore size of less than 100 microns, or less than 50 microns.

In one embodiment, the tissue connection devices comprise a non-woven electrospun fibrous mesh. In exemplary embodiments, the non-woven electrospun fibrous mesh comprises a fiber diameter from about 20 nm to about 2 microns. In another exemplary embodiment, the non-woven electrospun fibrous mesh comprises pore sizes ranging from about 200 nm to about 20 microns.

In one embodiment, the devices are biodegradable.

In another embodiment, the biological tissue is a tubular biological tissue, e.g., nerve, blood vessel, tendon, digestive tract, lymphatic, or genitourinary system tissue. An exemplary nerve tissue is peripheral nerve tissue. Exemplary genitourinary tissues are ureters or urethras.

In one embodiment, the device is for connecting biological tissue separated by 3 mm or less, or 1 mm or less.

In another aspect, the instant invention provides tissue repair devices comprising a membrane, wherein one side of the membrane comprises an adhesive, a temperature sensitive polymer, adhesive nanostructure, or a tissue-reactive compound.

In one embodiment, the membrane comprises one or more of biodegradable polyesters, poly(amino acids), poly(amino acid) derivatives, and natural polymers. Exemplary polyesters include poly(lactide), poly(glycolide), poly(s-caprolactone) and copolymers thereof. Exemplary natural polymers include chitosan, collagen, alginate esters, hyaluronic acid and derivatives thereof.

In one embodiment, the membrane is porous or non-porous.

In one embodiment, the tissue repair device is biodegradable. In one embodiment, the tissue repair device comprises a biodegradable foam or non-woven electrospun fibrous mesh.

In one embodiment, the tissue repair device is used in repairing a lacerated organs, e.g., liver, pancreas, heart or bladder, in one embodiment the repair device is for use in repairing tissue cut during surgical procedures, e.g., the dura.

In another aspect, the instant invention provides methods of connecting a tubular biological tissue, by attaching the first end of a first tubular devices described herein to one end of the tubular tissue, attaching the first end of a second tubular device to the other end of the tubular tissue, wherein the second end of the first and second tubular devices are attached to a donor tissue, thereby connecting the tubular biological tissue.

In one embodiment, the damaged, injured, or diseased portion of the tubular biological tissue has been removed. Exemplary tubular biological tissues include nerve, blood vessel, tendon, digestive tract, lymphatic, or genitourinary system tissue. An exemplary nerve tissue is peripheral nerve tissue. In one embodiment, the donor tissue is a graft. In another embodiment, the donor tissue is a sural nerve.

In another aspect, the instant invention provides methods of repairing biological tissue, by contacting the biological tissue in need of repair with a tissue repair device described herein, thereby repairing the biological tissue.

In one embodiment, the biological tissue is a lacerated organ, e.g., a liver, pancreas, heart or bladder. In another embodiment, the biological tissue is tissue that has been cut during a surgical procedure. An exemplary biological tissue is dura.

In another aspect, the instant invention provides kits comprising a tissue connection device described herein and instructions for use.

In another aspect, the instant invention provides kits comprising a tissue repair device described herein and instructions for use.

DESCRIPTION OF THE DRAWINGS

FIG. 1 shows a sutureless tissue connector. This version of the invention utilizes currently available, FDA-approved tissue adhesive to adhere each half of the connectors to the tissue to be repaired. In this example, the tissue repair is nerve repair.

FIG. 2 shows a sutureless blood vessel connector. This version of the invention utilizes currently available, FDA-approved tissue adhesives to adhere each half of the connectors to the tissue to be repaired. In this example, the blood vessel repair is arterial repair.

FIG. 3 shows a sutureless tendon connector. This version of the invention utilizes currently available, FDA-approved tissue adhesives to adhere each half of the connectors to the tissue to be repaired. In this example, the tissue repair is tendon repair.

FIG. 4 shows a sutureless digestive tract connector. This version of the invention utilizes currently available, FDA-approved tissue adhesives to adhere each half of the connectors to the tissue to be repaired. In this example, the tissue repair is small bowel repair, but it could be other elements of the digestive tract such as biliary or pancreatic duct, or large bowel.

FIG. 5 depicts a sutureless tissue connector with built-in tissue adhesive. This version of the invention is comprises of a biodegradable backbone and a coating of tissue adhesive material. The tissue adhesive can be temperature sensitive and form bonds at body temperatures or pH sensitive and become adhesive at neutral pH of the body fluids. In this example, the tissue repair is nerve repair.

FIG. 6 shows a sutureless tissue connector with built-in adhesive nanostructures. This version of the invention is comprises of a biodegradable backbone and a layer of tissue adhesive nanostructures mimicking the super-adhesive properties of Gecko feet. The layer of nanostructures mimicking Gecko feet can be made of a variety of biodegradable materials. In this example, the tissue repair is nerve repair.

DETAILED DESCRIPTION OF THE INVENTION

Figure 1:
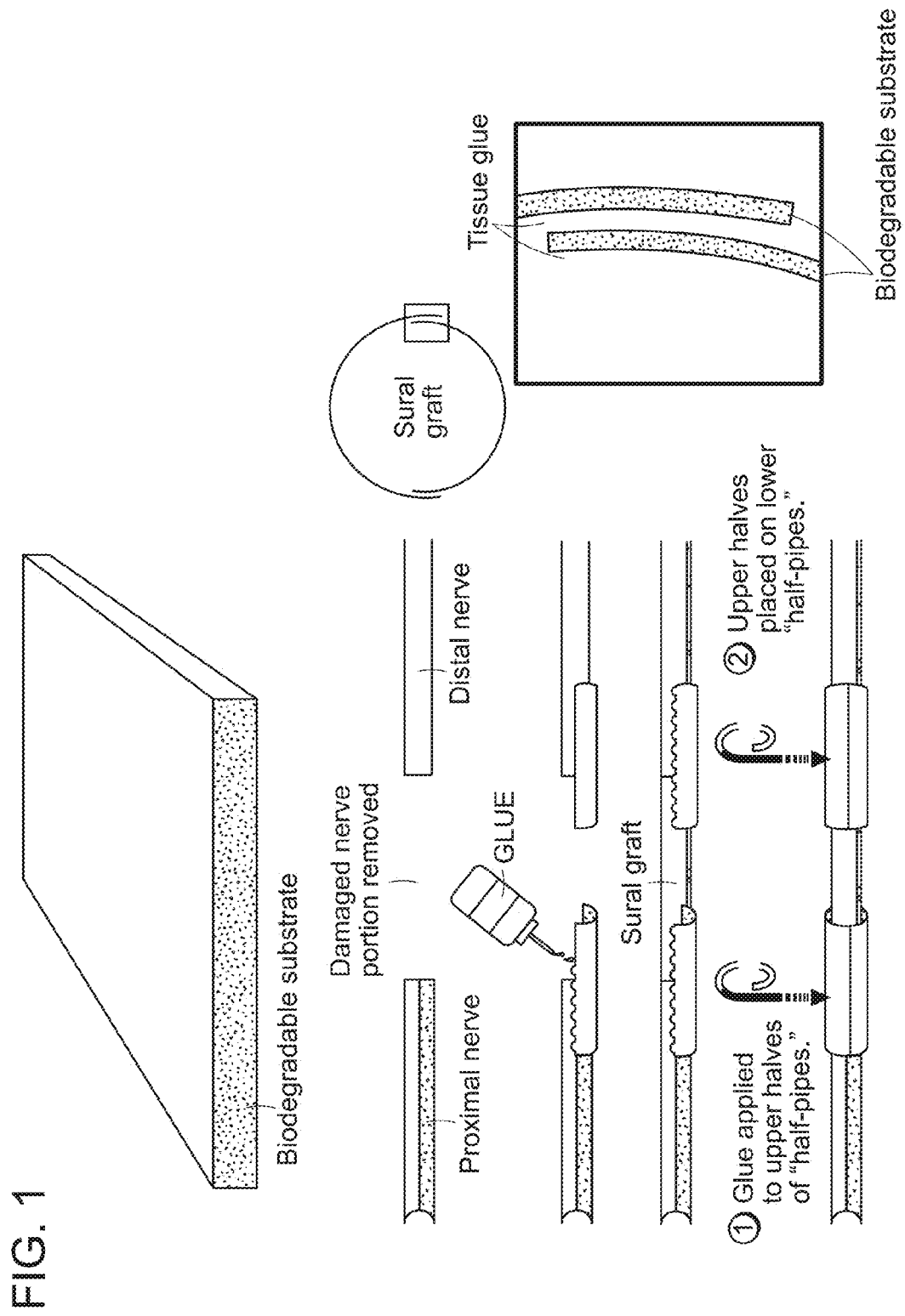
FIG. 1 depicts an embodiment of the invention as used to connect a nerve using a sural graft. Specifically.

The inventors of the instant application have developed novel compositions and methods for connecting biological tissue. Specifically, in at least one aspect, the inventors have developed biodegradable devices that can be used individually to join severed biological tissue assuming that the distance between the ends of the tissue is no greater than 3 mm, or can be used as pair along with a tissue graft to join biological tissue that is greater than 3 mm apart. The inventors have also developed a tissue repair device that can be used to repair tissue. Although the specification describes the tissue connection device in terms of a tubular tissue connection device, e.g., for connecting neurological tissue, one of ordinary skill in the art would realize that that the compositions of the invention can be used to join other biological tissue, such as those described herein, by altering the size or shape of the devices.

Devices

The devices described herein are useful for connecting biological tissue using while eliminating the need to use sutures. In one embodiment, the device comprises one or more tubular devices that can be used alone or in combination with a tissue graft to join biological tissue, e.g., severed biological tissue. In one embodiment, the devices comprise, for example, two half-tubular sections that can be used together to form an enclosed structure, such as a tube, around a biological tissue. In one embodiment, the sections are joined together with an adhesive so as to secure the tube-like shape.

The connection devices of the invention are made of, for example, a biodegradable material and can be made using a variety of materials and processes. In specific examples, the tissue connection device is comprised of biodegradable polymer. Exemplary polymers include polyesters, e.g. poly (lactide), poly(glycolide), poly(e-caprolactone) and their copolymers, poly(amino acid)s and their derivatives, natural biodegradable polymers, e.g., chitosan, collagen, alginate esters, hyaluronic acid, and their derivatives. Other biodegradable polymers and materials are contemplated for use in the compositions of the invention.

The thickness of the material forming the biological connector can range from 100 to 3000 µm. In exemplary embodiments, the thickness is 250 to 2000 µm or 500 to 1000 µm.

The inner diameter of the devices of the invention vary with the intended use. Depending on the type of tissue being connected, the interior diameter can be adjusted accordingly. In exemplary embodiments for use in repairing neurological tissue, e.g., peripheral nerve tissue, the inner diameter of the device ranges from 0.25 to 50 mm. Exemplary connection devices have an inner diameter of between 1 and 30 mm, or 2 and 20 mm, or 5 and 10 mm.

The connection devices can be made to be non-porous or porous. In exemplary embodiments, the connection devices can have with pore size of less than 100 µm, e.g., less than 50 µm. The non-porous connectors can be made from biodegradable membranes; and the porous connectors can be prepared from biodegradable foams and non-woven electrospun fibrous meshes.

As used herein, the term "electrospinning" is intended to mean a process that uses an electric field to draw a solution comprising, for example, a polymer or a ceramic from the tip of the capillary to a collector. A high voltage DC current is applied to the solution which causes a jet of the solution to be drawn towards the grounded collector screen. Once ejected out of the capillary orifice, the charged solution jet gets evaporated to form fibers and the fibers get collected on the collector. The size and morphology of the fibers thus obtained depends on a variety of factors such as viscosity of the solution, molecular weight, nature of the polymer or ceramic and other parameters regarding the electrospinning apparatus. The electrospinning process to form polymer nanofibers has been demonstrated using a variety of polymers (Huang, et al. Composites Science and Technology 2003; 63). Exemplary polymers used in electrospinning methods of the invention include those disclosed in U.S. Pat. No. 6,852,709, issued Feb. 8, 2005. Electrostatic spinning is a process by which polymer fibers of nanometer to micrometer size in diameters and lengths up to several kilometers can be produced using an electrostatically driven jet of polymer solution or polymer melt. The polymer solution or melt may comprise one or more therapeutically active molecules at concentrations determined by the ordinary skilled artisan.

As used herein, the term "uniaxial electrospinning" is intended to mean the electrospinning of a single electrospinning solution supply that is dispensed from a single spinneret.

As used herein, the term "coaxial electrospinning" is intended to mean the electrospinning of a single electrospinning solution supply that comprises of two different solutions that are physically separated from each other and that are dispensed from two separate spinnerets that share the same axis of symmetry.

As used herein, the term "multiaxial electrospinning" is intended to mean the electrospinning of a single electrospinning solution supply that comprises of multiple solutions that are physically separated from each other and that are dispensed through multiple spinnerets that share the same axis of symmetry.

As used herein, the term "polymer" generally includes, but is not limited to, homopolymers, copolymers, such as for example, block, graft, random and alternating copolymers, terpolymers, etc., and modifications thereof. In addition, unless otherwise specifically limited, the term "polymer" also includes all possible geometric, configurations of the molecule. In specific embodiments, the polymers used in the compositions of the invention are polyesters.

As used herein, the term "tube" is intended to mean composition of matter having an interior surface, and exterior surface, a lumen and openings on the two ends. The shape of the lumen may be modified to best conform to the tissue being connected. The tubes of the invention may be as described herein.

Another aspect of the invention provides tissue connection devices comprising an adhesive material on the interior surface of the device. This adhesive material allows for attachment of the device to the biological tissue in need of connection and/or to the graft used in certain embodiments of the invention. The layer of adhesive material can be manufactured of temperature-sensitive polymers, tissue adhesives, reactive groups, or biodegradable nanostructures that mimic the super-adhesive properties of Gecko feet (see, for example, Mandavi A, et al. *A biodegradable and biocompatible gecko-inspired tissue adhesive*. Proc Natl Acad Sci USA. 2008 Feb. 19; 105(7):2307-12.

Exemplary adhesives are fibrin glue, cyanoacrylate tissue adhesive, and albumin-glutaraldehyde glue. Exemplary temperature sensitive polymers are poly(N-isopropyl acrylamide), and pluronic copolymers. Exemplary tissue reactive groups are imido ester. N-hydroxylsuccinimide ester, epoxide, isocyanate, and aldehyde. Exemplary adhesive nanostructures are pillars comprised of biodegradable material, wherein the pillars comprise diameters in the range of 50 nm to 5 microns and lengths in the range of 10 microns to 2 mm. Exemplary reactive groups include aldehyde groups.

In another aspect, the instant invention provides tissue repair devices comprising a patch-like device for use in repairing torn, cut or ripped tissue. The tissue repair devices comprise a sheet of biodegradable polymer having an adhesive material on one side to allow for attachment to the tissue to be repaired. The adhesive material can be manufactured of temperature-sensitive polymers, tissue adhesives, reactive groups, or biodegradable nanostructures that mimic the super-adhesive properties of Gecko feet. The size and shape of the tissue repair device can be altered depending on the intended use and location of the device. The device can be made of the materials disclosed herein for the tissue connection devices.

Process

The devices of the invention can be made using a variety of processes, including for example, film casting, dip-coating, foaming, thermal press, and electrospinning.

In a film casting process, a polymer solution, e.g., a biodegradable polymer solution (1-20%, w/v) in organic solvent can be placed on a non-adhesive surface. The solvent is evaporated, and films can then cut into the desired shape and size. The films can then be hot-pressed in a mold of a desired shape at an appropriate temperature.

The device of the invention can be made by using an electrospinning process. For example, a solution of biodegradable polymer can be electrospun into random fiber meshes with fiber diameters ranging from 200 nm to 2 μm. The electrospun fiber mesh can be made into a desired shape. For example, for a tissue connection device, the fiber mesh can be electrospun onto a mandrel. In certain embodiments, the tube can be removed from the mandrel and sliced open with a single cut to yield an open composition, which is then cut into the desired length. The thickness of the device can be controlled by the duration of electrospinning as known to those of ordinary skill in the art.

The electrospun composition can be further strengthened by dip-coating a thin layer of polymer solution, or electrospraying a thin polymer film, which is subsequently dried and acts as a binder layer to fuse the electrospun fibers.

Surface reactive groups, such as aldehyde groups, can be added to a surthce of the devices through plasma or UV-initiated surface grafting techniques. For example, a thin layer of poly(acrylaldehyde) can be grafted by UV treatment of a surface and coating it with aqueous solution of acrylaldehyde or acrolein, Methods of the Invention The devices of the invention are useful for the connection or repair of biological tissue. In one embodiment, the tissue connection devices of the invention are useful for connecting tubular biological tissue, such as peripheral and cranial nerves, blood vessels, tendons, lymphatic vessels, digestive tract including biliary and pancreatic ducts and small and large bowels, and genitourinary tract including ureters and urethra.

The term "treated," "treating" or "treatment" includes the diminishment or alleviation of at least one symptom associated or caused by the state, disorder or disease being treated. For example, treatment includes the partial or complete regeneration of nerve fibers in a subject.

The term "subject" is intended to include organisms needing treatment. Examples of subjects include mammals, e.g., humans, dogs, cows, horses, pigs, sheep, goats, cats, mice, rabbits, rats, and transgenic non-human animals. In certain embodiments, the subject is a human.

In another embodiment of the invention, the tissue repair devices of the invention are useful for repairing tissues such as lacerated organs. Exemplary organs include a liver, pancreas, heart, kidney, bladder, or dura. The organs can be lacerated traumatically or surgically.

Exemplary surgical procedures used in the methods of the invention are described, for example, in Hadlock et al., Archives of Otolaryngology—Head & Neck Surgery 124: 1081-1086, 1998; WO 99/11181; U.S. Pat. No. 5,925,053; WO 88/06871; Wang et al., Microsurgery 14:608-618, 1993; and Mackinnon et al., Plast. Reconst. Surg. 85:419-424, 1990.

Figure 2:
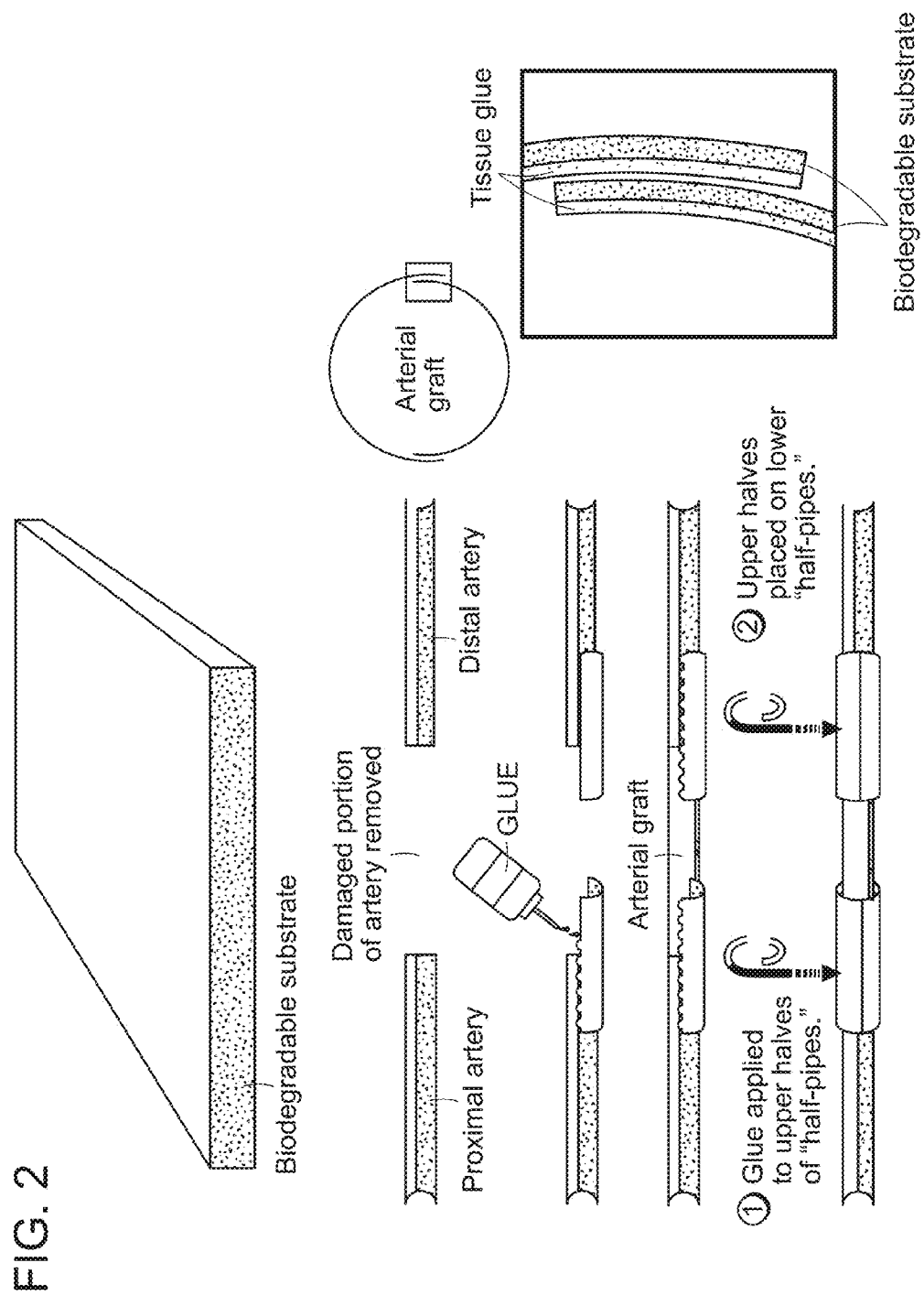
FIG. 2 depicts an embodiment of the invention as used to connect a blood vessel using an arterial graft. Specifically.
Figure 3:
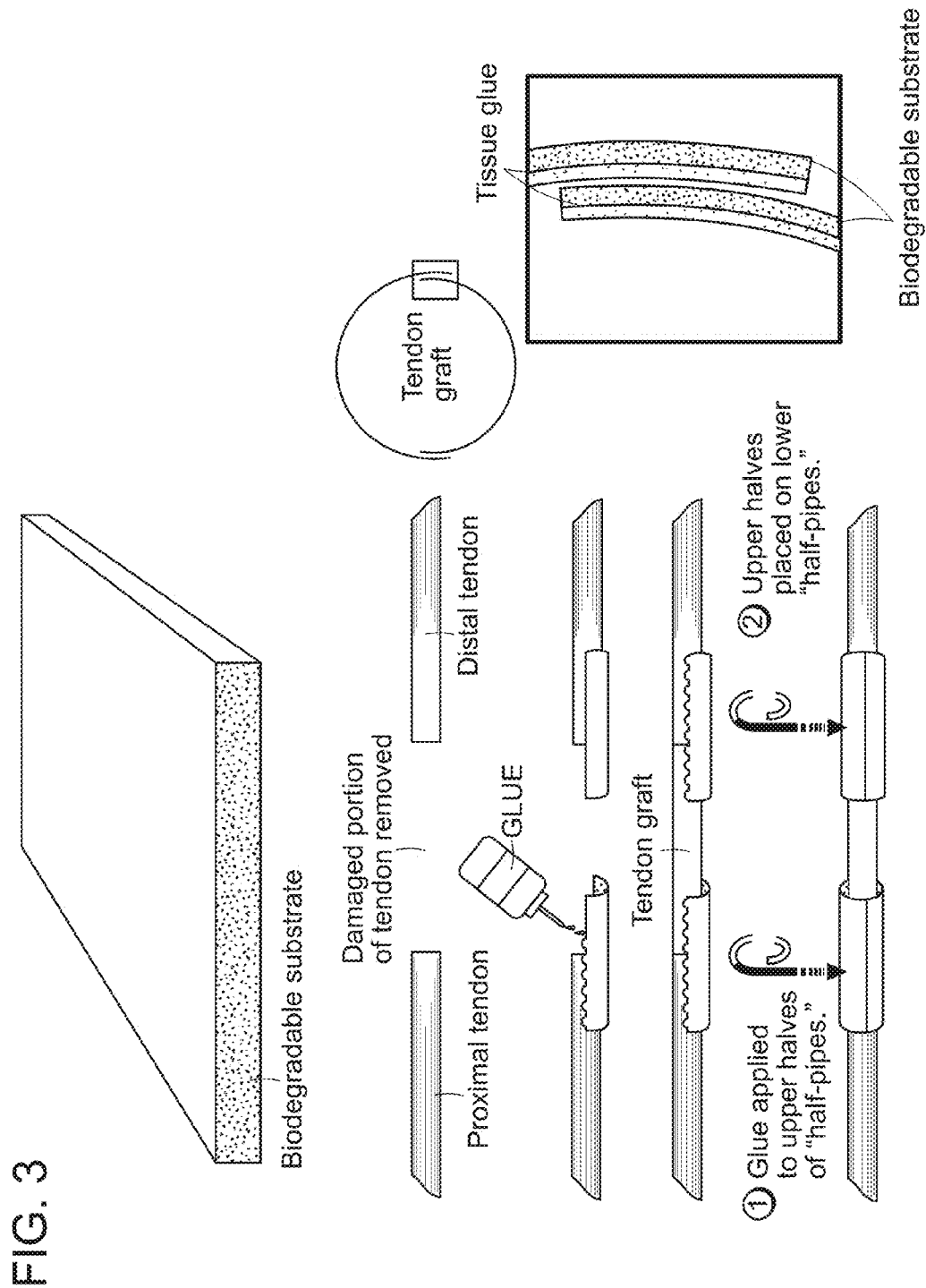
FIG. 3 depicts an embodiment of the invention as used to connect a tendon using a tendon graft. Specifically.
Figure 4:
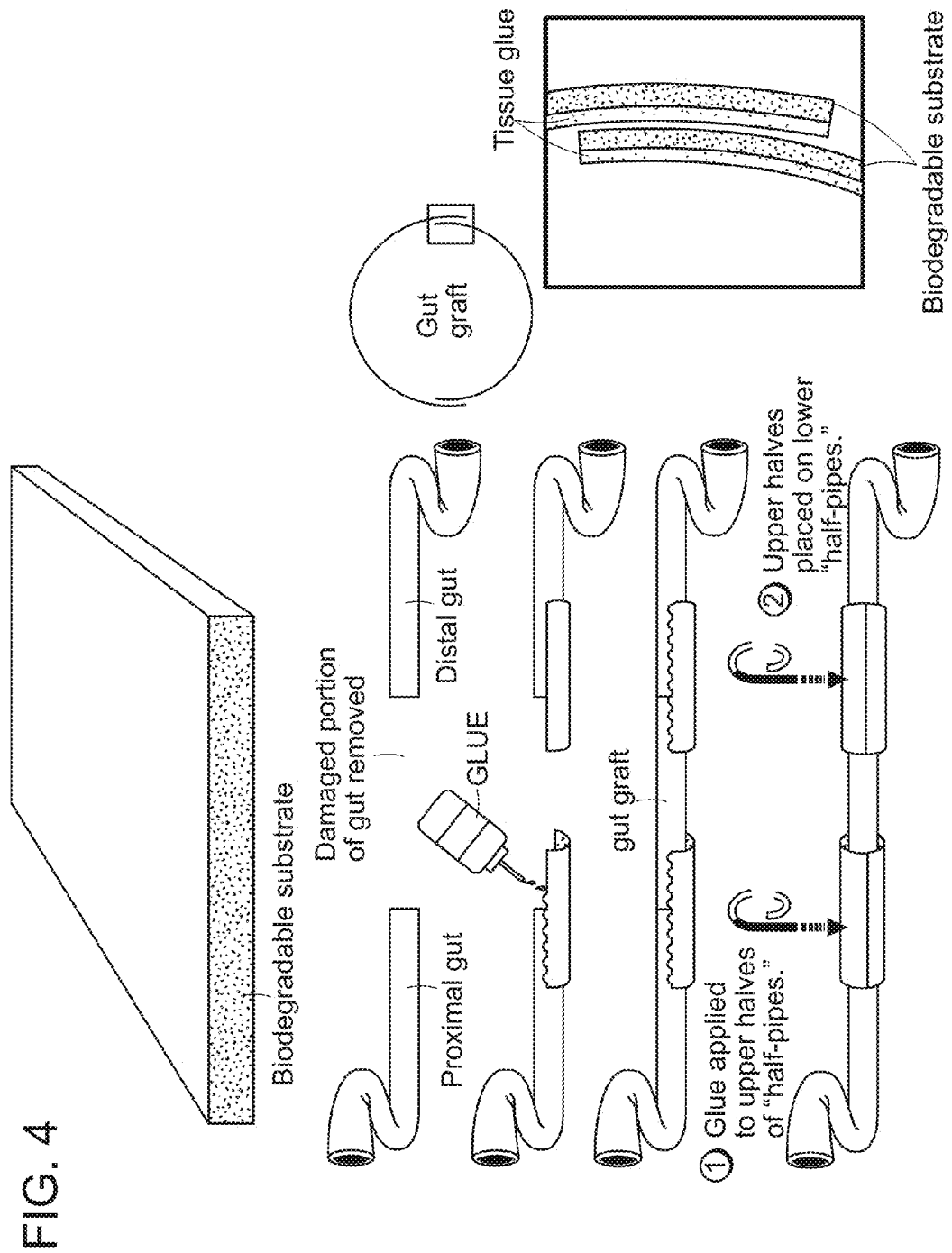
FIG. 4 depicts an embodiment of the invention as used to connect the bowel using a gut graft. Specifically.

An example of peripheral nerve repair is shown in FIG. 1, A similar approach is applicable to repair of all tubular biological tissue such as blood vessels (FIG. 2), tendons (FIG. 3), digestive tract (FIG. 4), lymphatic vessels and genitourinary system (e.g. ureters, urethra).

A surgeon or medical processional can use the devices of the invention to repair biological tissue or connect biological tissue as necessary. The tissue connection device of the invention allows adhesion of tissues over a large surface area and reduce tension at sites of repair. The use of the devices of the invention are preferable to sutures because the tension created at the suture site is distributed to over a larger surface area, reducing risk of suture failure.

In one embodiment, the tissue connection device of the invention can be used to connect biological tissue that has been damaged, severed or diseased. In one embodiment, biological tissue that requires connection and is close in proximity is connected using one tissue connection device of the invention. For this use, a medical professional can insert the ends of the biological tissue into a device of the invention. The professional may use an adhesive to attach the device to the biological tissue, or may use a device of the invention comprising a tissue adhesive disclosed herein. In certain embodiments, the device of the invention is prepared in sections that are joined around the biological tissue and secured in place with a biological adhesive.

For applications where the tissue in need of connection is a greater distance than can be connected by a single tissue connection device of the invention, two devices can be used in connection with donor tissue, e.g., a graft. As used herein, the term "graft" refers to any tissue or tissue replacement intended for implantation within a human or animal. Various types of graft are encompassed within the subject invention, such as autografts, syngrafts, allografts, and xenografts. The size (e.g., length and diameter) of the graft is not critical the invention and can be adjusted as necessary to be of proper length to connect the tissue. The graft may be natural or engineered from synthetic materials.

Figure 5:
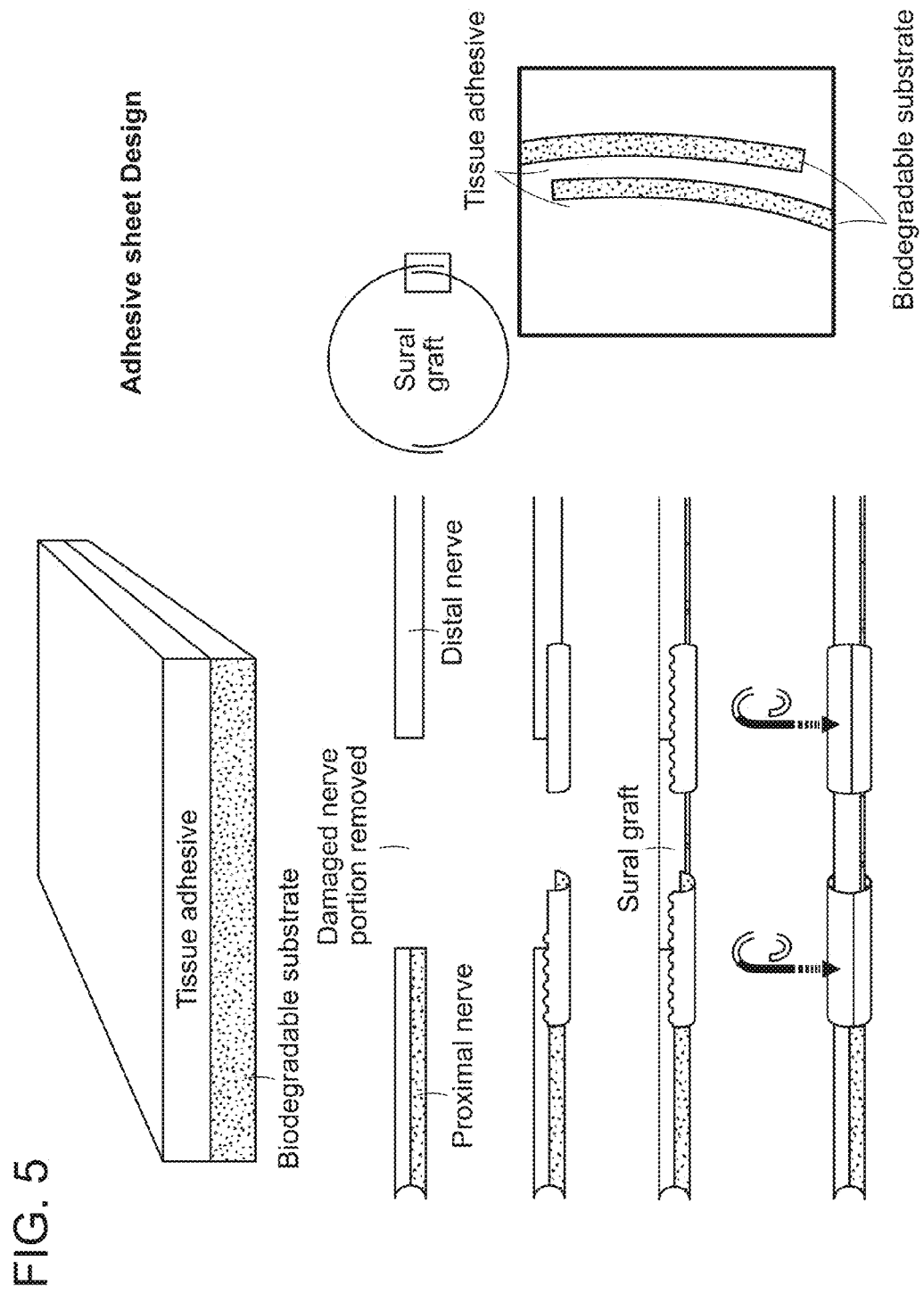
FIG. 5 depicts an embodiment of the invention as used to connect a nerve using a sural graft. This figure depicts the use of a tissue adhesive coating the device of the invention. Specifically.
Figure 6:
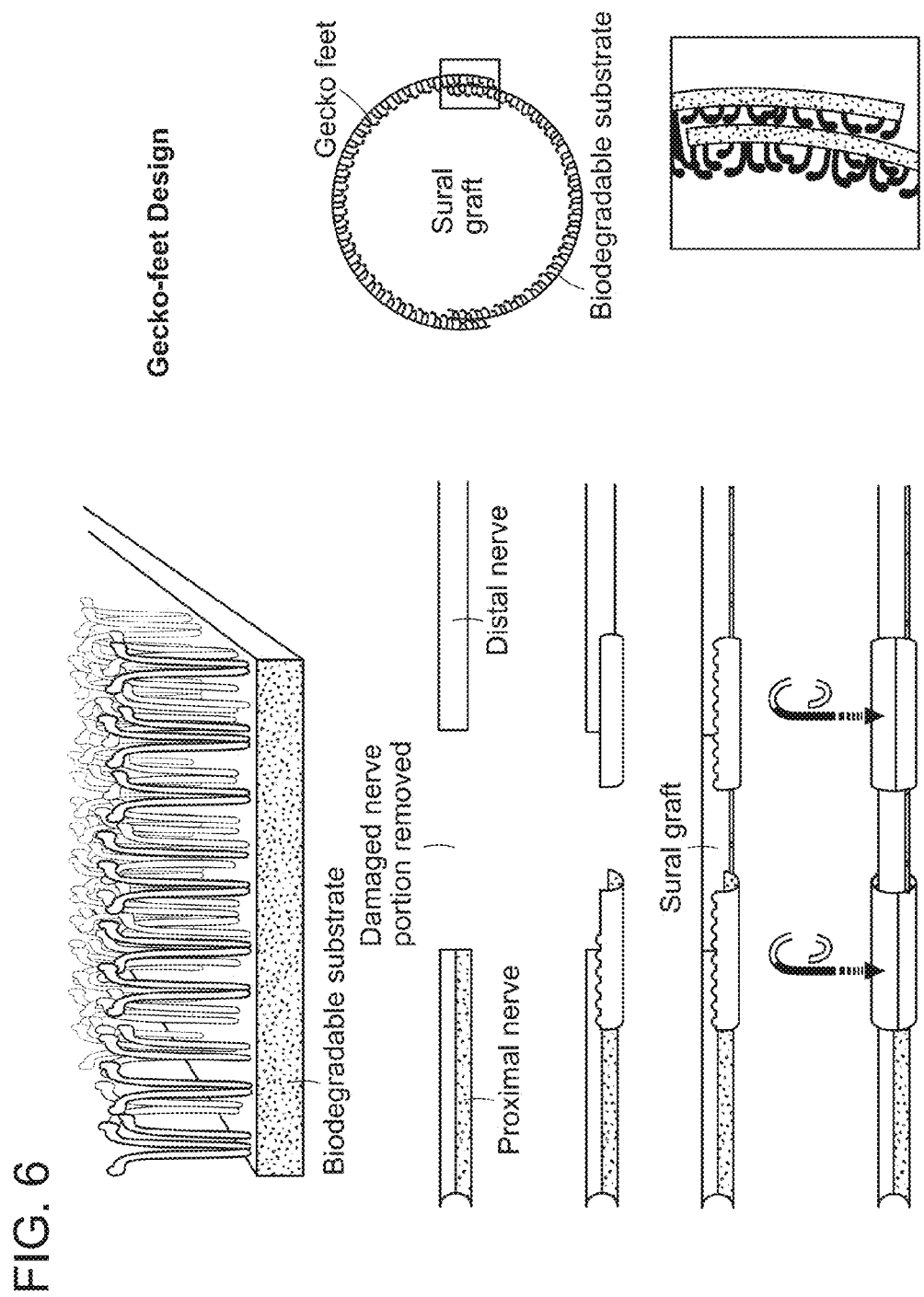
FIG. 6 depicts an embodiment of the invention as used to connect a nerve using a neural graft. This figure depicts the use of adhesive nanostructures coating the interior of the device of the invention. Specifically.

Examples of nerve repair are illustrated in FIGS. 1, 5 and 6, a first section of a tissue connection device is placed under the nerve, the nerve graft to be repaired is lowered onto the connection device, and the nerves is aligned and then a second section of the connection device is placed onto the nerve. Examples of blood vessel repair (FIG. 2), tendon repair (FIG. 3) and digestive tract repair (FIG. 4) are also shown and occur in similar fashion.

Tissue repair devices of the invention are applied to the tissue, e.g., an organ, in need of repair. The device is held in place until the tissue adhesive adheres the device to the tissue, thereby allowing for repair of the tissue.

EXAMPLES

It should be appreciated that the invention should not be construed to be limited to the examples that are now described; rather, the invention should be construed to include any and all applications provided herein and all equivalent variations within the skill of the ordinary artisan.

Example 1

Repair of the Sciatic Nerve in a Rat Model

To make the devices for use in this example, poly(caprolactone) (PCL) was dissolved at 14% (w/w) in a solvent consisting of 90% dichloromethane and 10% N,N-dimethylformamide (v/v) overnight at room temperature using a rotary shaker. Using a syringe pump, this solution was fed through a 1 cc syringe fitted with a 27 G needle at a rate of 2 mL/hr and electrospun onto a rotating 1 mm brass mandrel. Electrospinning was initiated by applying a positive electric field of 10 kV to the needle tip using a high voltage power supply. A negative electric field of 6 kV was applied to the mandrel, which was located at a distance of 10 cm from needle tip. The syringe pump was mounted onto a motorized X-Y stage that swept back and forth along the length of the mandrel at a speed of 10 mm/s for a total of 25 cycles in order to ensure even deposition of the fibers. The tube was then washed in 100% ethanol and dried thoroughly to remove all traces of organic solvent. To improve its mechanical integrity, the tube (still mounted on the mandrel) was heat-treated in a 55° C. water bath for a period of 30 minutes. This purpose of this heat-treatment step is to partially melt and fuse the PCL fibers; it may be omitted if necessary. Upon completion of the heat-treatment step, a razor blade was used to make a single cut through the wall of the tube along its long axis. The tube was then removed from the mandrel.

The following example demonstrates the use of the connection device of the invention in a rat model of a severed sciatic nerve.

Figure 7:
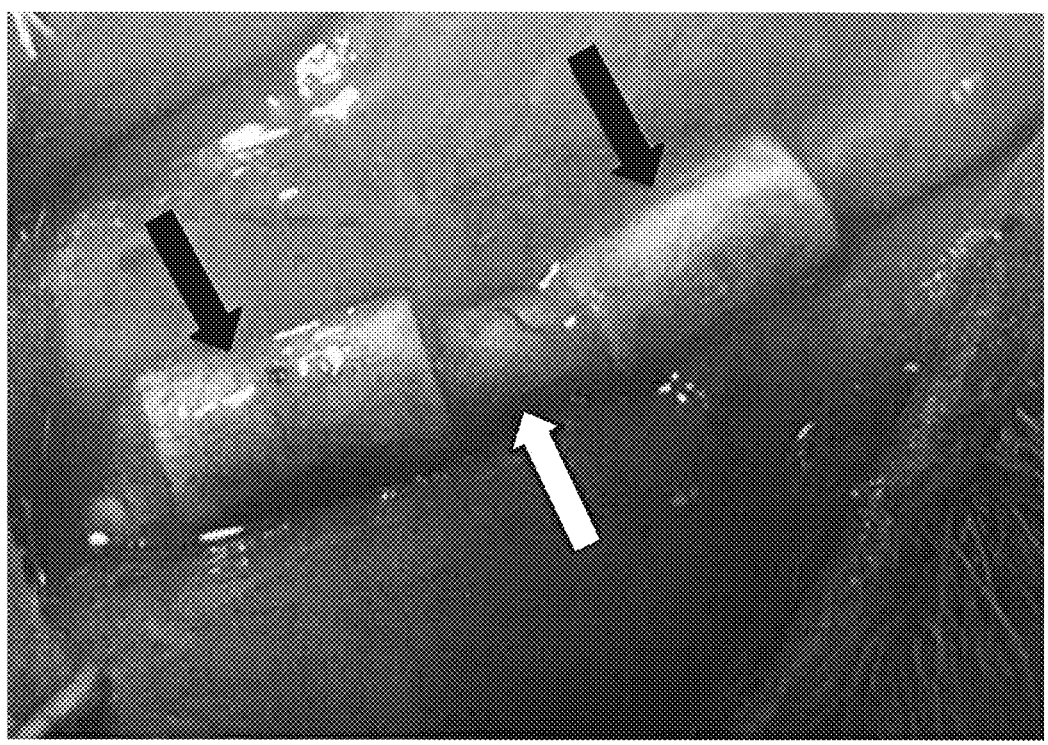
FIG. 7 depicts a photograph showing the use of a tissue connection device of the invention used in a rat model of a severed sciatic nerve.

A 10 mm segment of the rat sciatic nerve was removed through an incision in mid-thigh and an allograft of 10 mm sciatic nerve was transplanted from another rat. Instead of using sutures to connect the nerves, each end of the host and graft were connected using a tissue connection device and fibrin-based glue. FIG. 7 shows the use of the tissue connection device; of the solid arrows point to the nerve cuffs and outlined arrows indicate the grafted sciatic nerve.

Figure 8:
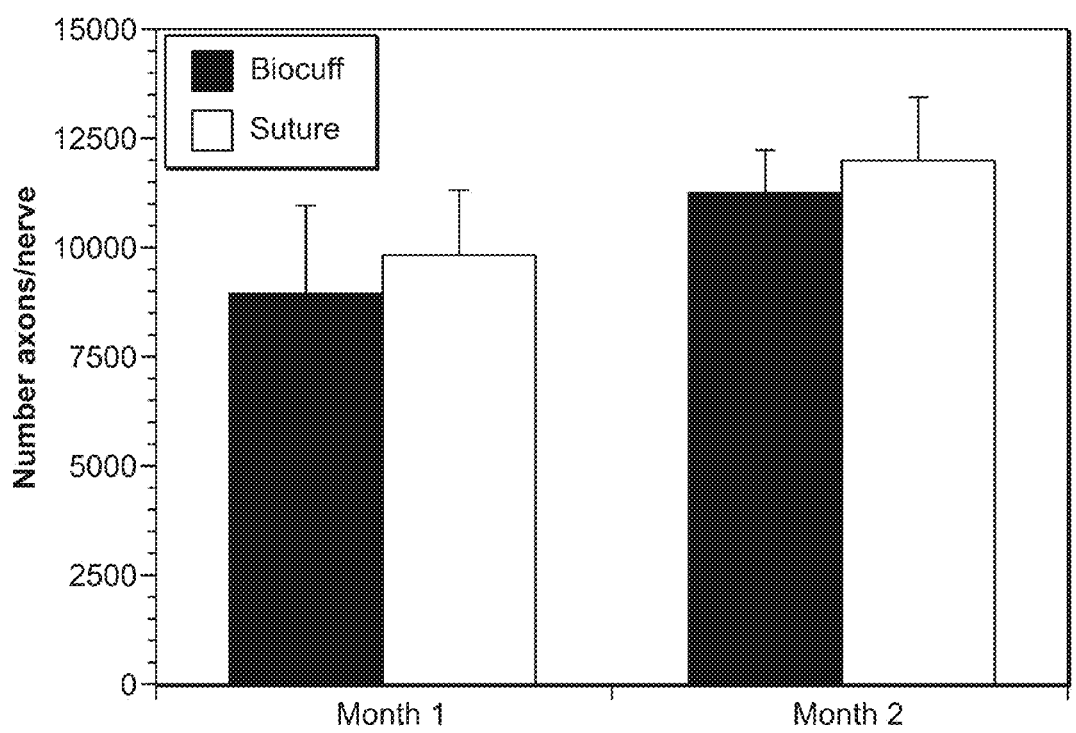
FIG. 8 depicts a graph showing the numbers of regenerated axons in sciatic nerves repaired using the devices of the invention and using the conventional suture techniques after 1 or 2 months.

In order to determine the efficacy of repairing the damaged sciatic nerves using the devices depicted in FIG. 7, a similar rat model was repaired by using an allograft as shown in FIG. 1 and suturing the ends using three 10-0 sutures. After 1 or 2 months, sciatic nerves distal to the graft were harvested, fixed and processed for plastic sectioning. Numbers of regenerated axons were counted in cross sections of Toluidine-blue stained sciatic nerves (n=4/group at each time points). There were no statistically significant differences between the suture and tissue connection device groups, thereby demonstrating the efficacy of the devices of the invention (See FIG. 8).

Incorporation by Reference

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A sutureless tissue connection device for connecting biological tissue, comprising:
   a first tubular device comprising a first and a second end;
   a second tubular device comprising a first and a second end;
   wherein one end of the first and second tubular devices is adapted to attach to the ends of the biological tissue, and the other ends of the first and second tubular devices is adapted to attach to donor tissue, and
   wherein the first and second tubular devices comprise two separate half-tubular sections each section having an interior surface with an adhesive, a temperature sensitive polymer, adhesive nanostructure, or tissue-reactive groups formed thereon that assembles having an interior surface of a first half-tubular section disposed to overlap and bond to an exterior surface of a second half-tubular section at two diametrically opposed edges to form the sutureless tissue connection device.

2. The sutureless tissue connection device of claim 1, wherein the two sections are connected, or partially connected, along the length of one side of the sections.

3. The sutureless tissue connection device of claim 1, wherein the tubular devices comprise a biodegradable substrate.

4. The sutureless tissue connection device of claim 1, wherein the adhesive is selected from the group consisting of fibrin glue, cyanoacrylate tissue adhesive, and albumin-glutaraldehyde glue.

5. The sutureless tissue connection device of claim 1, wherein the temperature sensitive polymer is selected from the group consisting of poly(N-isopropyl acrylamide), and Pluronic copolymers.

6. The sutureless tissue connection device of claim 1, wherein the tissue reactive group is selected from the group consisting of imido ester, N-hydroxylsuccinimide ester, epoxide, isocyanate, and aldehyde.

7. The sutureless tissue connection device of claim 1, wherein the adhesive nanostructures are pillars comprised of biodegradable material.

8. The sutureless tissue connection device of claim 1, wherein the biological tissue is a tubular biological tissue.

9. The sutureless tissue connection device of claim 8, wherein the tubular biological tissue is selected from the group consisting of nerve, blood vessel, tendon, digestive tract, lymphatic, or genitourinary system tissue.

10. The sutureless tissue connection device of claim 9, wherein the nerve tissue is peripheral nerve tissue.

11. The sutureless tissue connection device of claim 9, wherein the genitourinary tissue is a ureter or urethra.

12. A method of connecting a tubular biological tissue, comprising:

providing a first tubular device and a second tubular device of claim 1;

attaching the first end of the first tubular device to one end of the tubular tissue;

attaching the first end of the second tubular device to the other end of the tubular tissue;

wherein the second end of the first and second tubular devices are attached to a donor tissue;

thereby connecting the tubular biological tissue.

13. A kit comprising the sutureless tissue connection device of claim 1 and instructions for use.

14. A kit comprising the sutureless tissue repair device of claim 13 and instructions for use.

\* \* \* \* \*